US00PP25981P3

(12) United States Plant Patent
Lugli et al.

(10) Patent No.: US PP25,981 P3
(45) Date of Patent: Oct. 13, 2015

(54) CHERRY TREE NAMED 'PA4UNIBO'

(50) Latin Name: *Prunus avium*
Varietal Denomination: PA4UNIBO

(71) Applicant: Alma Mater Studiorum-Università degli Studi di Bologna, Bologna (IT)

(72) Inventors: Stefano Lugli, Modena (IT); Riccardo Correale, Bologna (IT); Michelangelo Grandi, Castenaso (IT)

(73) Assignee: Alma Mater Studiorum-Università degli Studi di Bologna, Bologna (IT)

( * ) Notice: Subject to any disclaimer, the term of this patent is extended or adjusted under 35 U.S.C. 154(b) by 129 days.

(21) Appl. No.: 13/986,704

(22) Filed: May 28, 2013

(65) Prior Publication Data

US 2013/0326774 P1 Dec. 5, 2013

(30) Foreign Application Priority Data

May 25, 2012 (QZ) ..... PBR 2012/1160

(51) Int. Cl.
*A01H 5/00* (2006.01)
*A01H 5/08* (2006.01)

(52) U.S. Cl.
USPC ..... Plt./181
CPC ..... *A01H 5/085* (2013.01)

(58) Field of Classification Search
USPC ..... Plt./181
See application file for complete search history.

*Primary Examiner* — Annette Para

(74) *Attorney, Agent, or Firm* — Hershkovitz & Associates, PLLC; Abraham Hershkovitz

(57) ABSTRACT

*Prunus avium* 'PA4UNIBO' is a novel cherry tree derived from a seedling of unknown cross which was planted at Vignola, Modena Province, Italy. It was initially propagated by grafting to root stocks of varying vigor and, after testing in districts and plantings of differing types, proved to have the qualities proper to a promising new cultivar for the market.

5 Drawing Sheets

Latin name of the genus/species of the plant claimed (cultivar): *Prunus avium.*

Variety denomination: PA4UNIBO.

CROSS-REFERENCE TO RELATED APPLICATIONS

This application claims priority of pending EU Plant Patent for 'PA4UNIBO' which was filed on 25 May 2012 as Application No. 2012/1160 in the name of Applicant (holder) Alma Mater Studiorum—Università degli Studi di Bologna, the entire contents of which are expressly incorporated herein by reference. EU Trademark for 'Sweet Valina' was released on 2 Jan. 2013 as Registration No. 011058609 of Applicant (holder) Alma Mater Studiorum—Università degli Studi di Bologna. Such European Trademark is associated to PA4UNIBO and used to distinguish such cherry variety from the others.

FIELD OF THE INVENTION

*Prunus avium* 'PA4UNIBO' is derived from seedling of unknown cross and originally called Selection DCA BO B5D23 which was planted at Vignola, Modena Province, Italy, in February 2002 and first cropped in 2004. It was initially propagated by grafting to root stocks of varying vigor and, after testing in districts and plantings of differing types, proved to have the properties proper to a promising new cultivar for the market. It picks in the first decade of June to the end of June in Modena Province, approximately 18-20 days after 'Burlat' and about 2 days after 'Bing', at about the same harvest date of the variety known as 'Summit'.

SUMMARY OF THE INVENTION

The parentage of the variety is unknown. The name of a variety of a comparable harvest date is 'Summit'. However, compared to 'Summit', 'PA4UNIBO' has larger fruit (caliber of 32-34 mm prevailing) of firmer flesh, more uniform ripening and higher sugar content. 'PA4UNIBO' was selected for its high qualities, including tree growth and yield performance, and fruit appearance and excellent taste-flavor properties, very sweet and with a good level of acidity. Its other most distinctive traits include mid-season, uniform ripening and large, firm-fleshed fruit that is aromatic and bright red (scale 4 CTIFL). The date of discovery/cross was in the year 2000. The location of the discovery was Vignola, Modena Province, Italy. The date of the first asexual propagation was in 2008 in Vignola, Modena Province, Italy. 'PA4UNIBO' was initially propagated on root stock of 'Colt' (U.S. Plant Pat. No. 4,059) in the trial fields of Bologna University to test its field and yield performance in a traditional orchard planting system.

BRIEF DESCRIPTION OF THE DRAWINGS

The accompanying photographs show typical specimens of the new variety as depicted in color as nearly true as is reasonably possible in color illustrations of this character.

DETAILED BOTANICAL DESCRIPTION OF THE VARIETY

Figure 1:
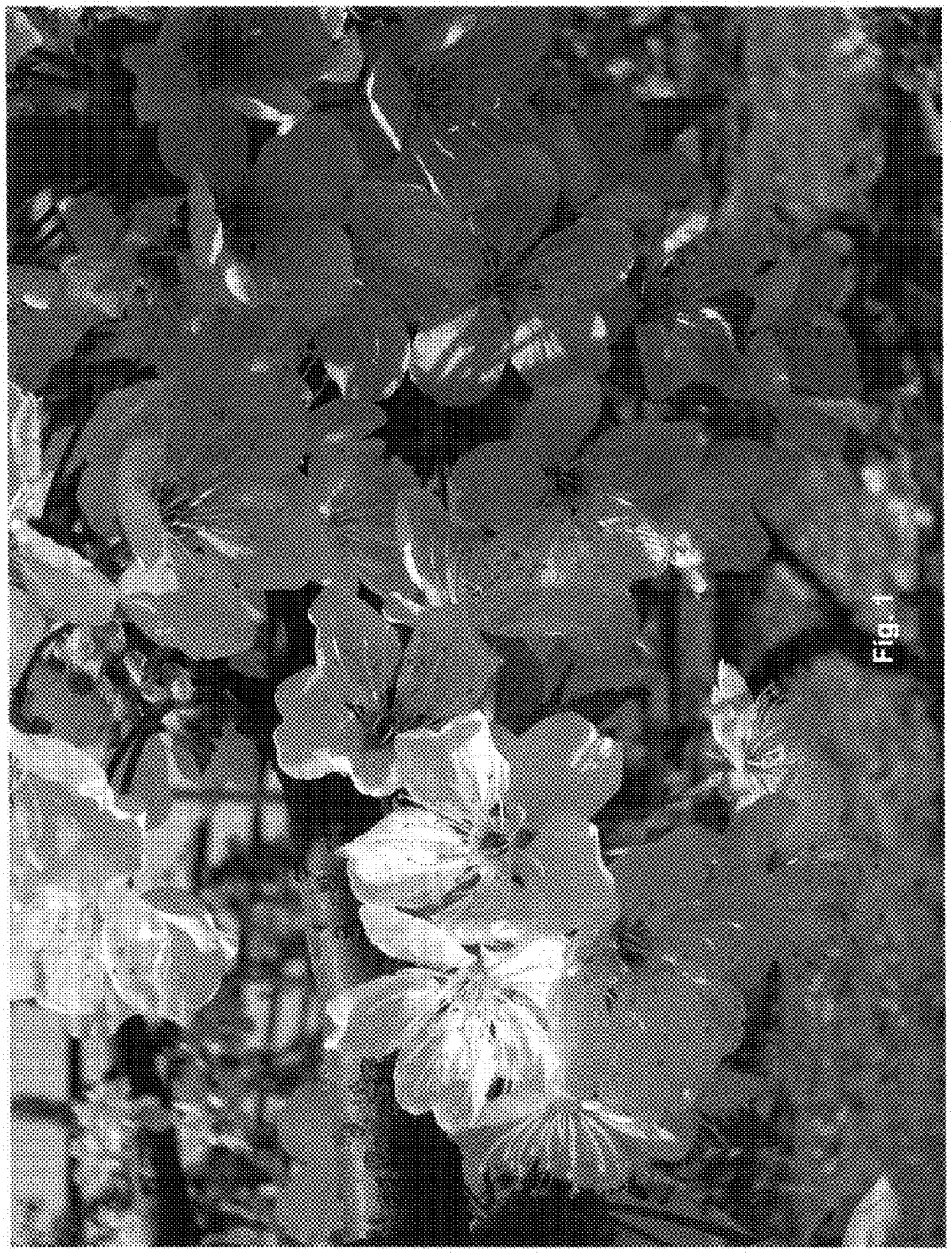
FIG. 1 illustrates the detail of fully-open blossoms of PA4UNIBO.
Figure 2:
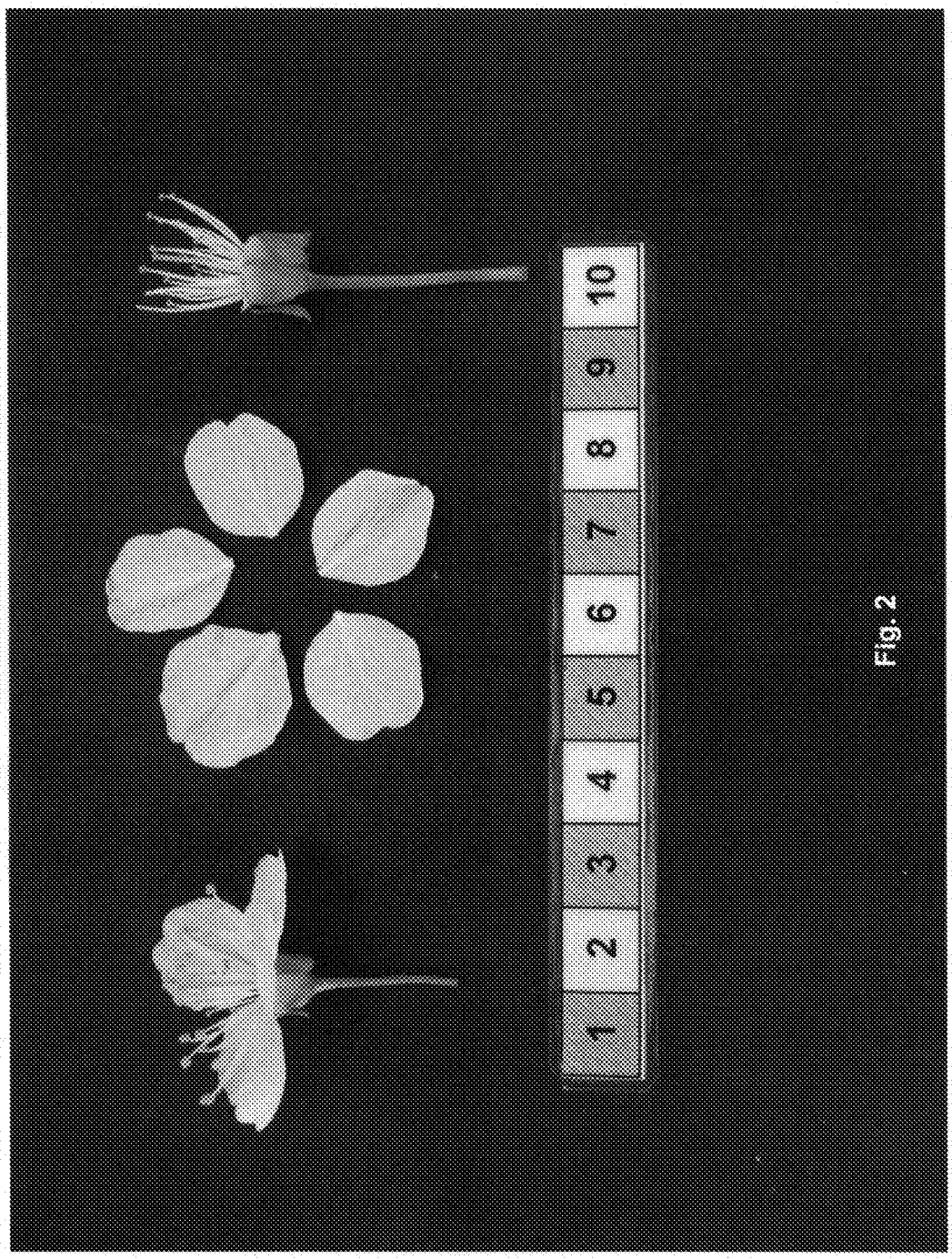
FIG. 2 is the flower, full front, in profile and with separated petals, of PA4UNIBO.
Figure 3:
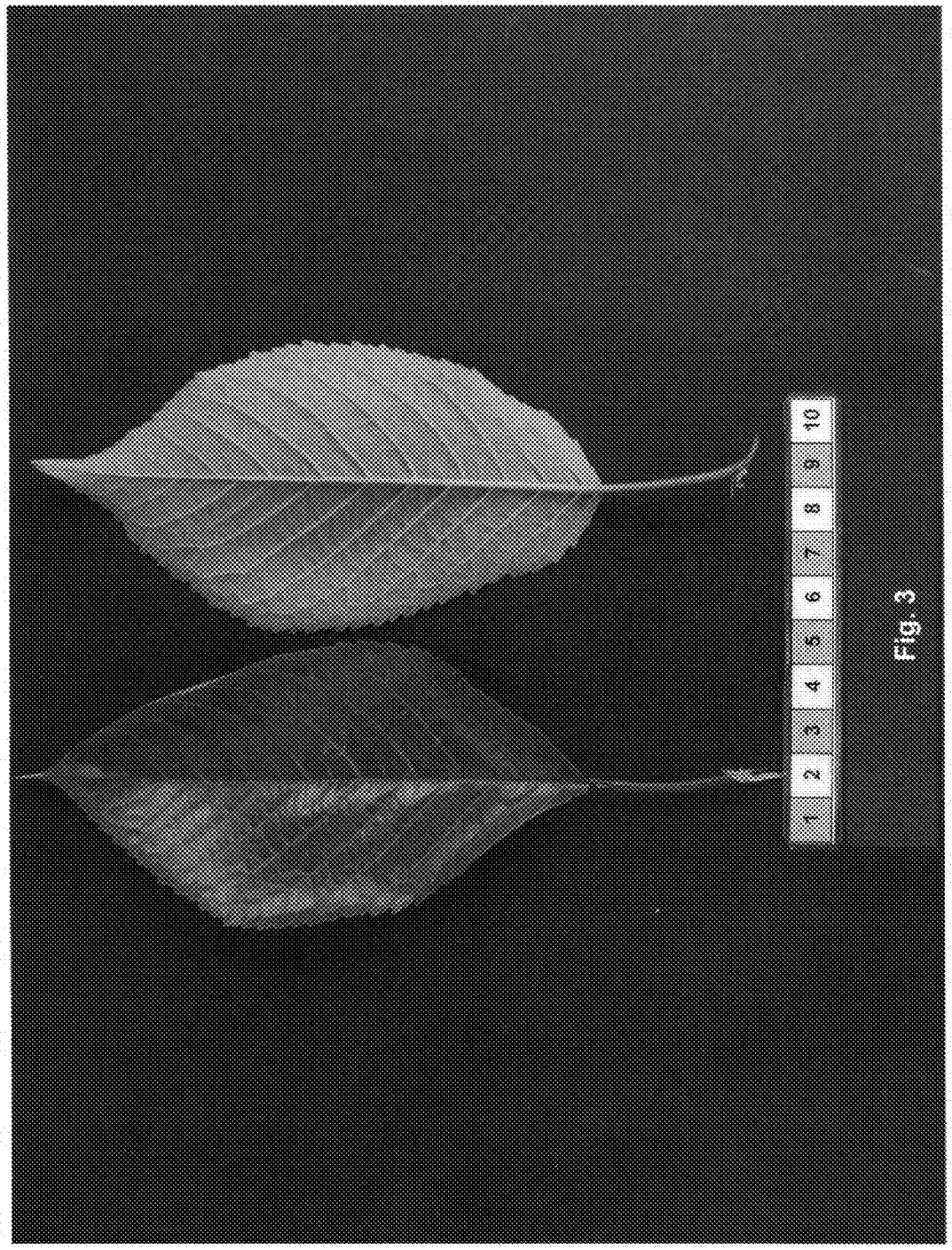
FIG. 3 shows the leaf profile of PA4UNIBO. Two leaves have been detached and one has been placed upper leaf surface side down to show the lower leaf surface details.
Figure 4:
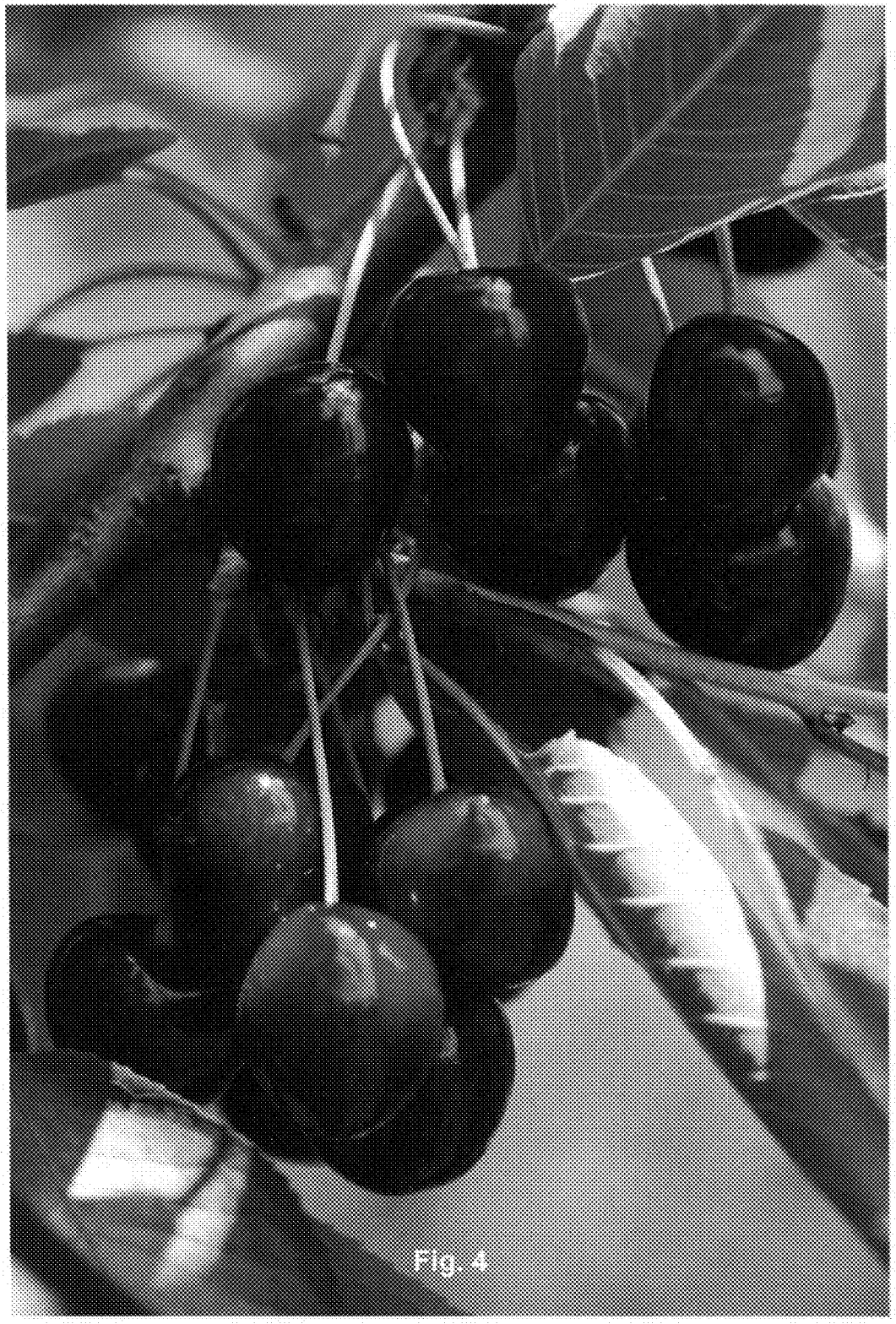
FIG. 4 illustrates the details of a fruit cropping, including an example measurement, of PA4UNIBO.
Figure 5:
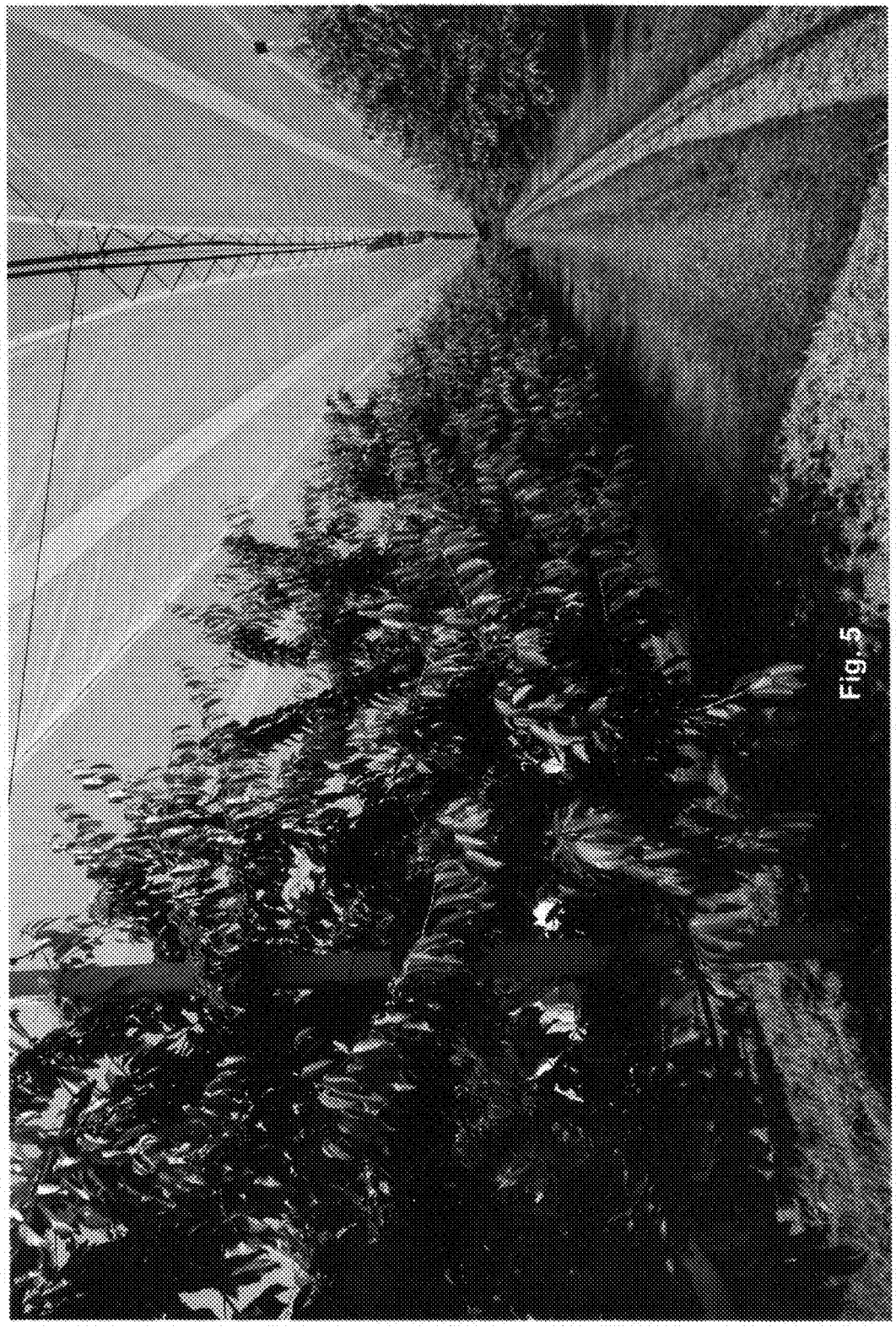
FIG. 5 shows the tree architecture of PA4UNIBO with width-spread and height.

General:
- *Age of described tree.*—5 years, drapeau (flag) training system.
- *Location of described tree.*—Vignola, Modena Province, Italy.
- *Name of color chart used.*—Royal Horticultural Society Colour Chart.
- *Name of root stock.*—'Colt'.

Tree:
- *Vigor.*—High.
- *Height.*—3.5-4 meters.
- *Spread.*—3 meters.
- *Growth habit.*—Semi-open.
- *Canopy density.*—Medium.
- *Trunk diameter at specified height.*—15-18 cm diameter, as measured at about 5 cm above graft joint cm above graft joint.
- *Trunk color.*—Reddish (200D) with a few grayish flecks (201A).
- *Bark texture.*—Of average roughness.
- *Tendency toward alternate bearing.*—No.
- *Winter hardiness.*—Unknown; no winter cold damage found in this Po Valley district.
- *Chilling requirement.*—Unknown.

Branch:
- *Length.*—250-310 cm of main branches.
- *Diameter.*—11-13 cm at basal part of main branches.
- *Crotch angle.*—70-80° depending on training system.
- *Bark color.*—Reddish (200D).
- *Bark texture.*—Of average roughness.

Current year shoot:
- *Length.*—60-80 cm.
- *Color.*—Reddish (200D) with uneven grayish overtone (201A).

Winter hardiness:
- *USDA hardiness zone.*—Unknown.
- *Chilling requirement.*—Unknown.

Flower buds:
- *Number per spur.*—4-5, mostly 4.
- *Shape.*—Ovoid.
- *Length.*—About 1 cm.
- *Diameter.*—Under 1 cm.
- *Color.*—Redish perules (187C).

Flowers:
- *Number per cluster.*—Minimum of 10-maximum 16 per spur, 2-3 per bud. Abundant bloom.
- *Relative position of petals.*—Slightly overlapping petals.
- *Diameter.*—37-41 mm.
- *Depth.*—17-20 mm, as measured from receptacle to maximum petal aperture.
- *Is pollen produced?.*—Yes.
- *Coloration of pollen.*—Pale yellow (12A).

Sepal:
- *Length.*—5-7 mm.
- *Shape.*—Conical.
- *Width.*—About 5 mm.
- *Apex.*—Pointed.
- *Base.*—Pointed.
- *Margin descriptors.*—Regular margin.
- *Color — upper surface.*—Green (139C).
- *Color — lower surface.*—Green (139C).

Petals:
- *Number per flower.*—5.
- *Shape.*—Circular.
- *Length.*—17-19 mm.
- *Width.*—15-17 mm.
- *Apex.*—Slightly sunken.
- *Base.*—Slightly pointed.
- *Margin.*—Slightly undulated.
- *Color — upper surface.*—White (155B).
- *Color — lower surface.*—White (155B).

Bloom:
- *Date of bud burst.*—7-8 Apr. 2013.
- *Date of first bloom.*—14 Apr. 2013.
- *Date of full bloom.*—17 Apr. 2013.

Pedicel:
- *Length.*—33-41 mm.
- *Diameter.*—1.2-1.4 mm.
- *Color.*—Green (143B).

Pistil:
- *Quantity.*—1.
- *Size.*—18-21 mm.
- *Color.*—Green (143C).

Anthers:
- *Quantity.*—27-30 of length from 5-15 mm usually positioned slightly below top of the stigma; 4-5 anthers in each flower are of the same length or slightly longer than the top of the stigma. White filament (155D).
- *Size.*—Under 1 mm diameter.
- *Color.*—Orange-yellow (15A).

Stigma:
- *Quantity.*—1.
- *Size.*—1.1-1.3 mm diameter.
- *Color.*—Green (142A).

Styles:
- *Quantity.*—1.
- *Size.*—14-15 mm length.
- *Color.*—Pale white-green (142C) turning rosé (36C) toward end of bloom.

Ovary/ies:
- *Quantity.*—1.
- *Size.*—4-6 mm.
- *Color.*—Green (143C).

Leaves:
- *Length.*—11.8-13.1 cm.
- *Width.*—6.8-8.0 cm.
- *Shape.*—Elliptical.
- *Apex shape.*—Pointed.
- *Base shape.*—Pointed.
- *Margin.*—Fine-toothed.
- *Color — upper surface.*—Green (137A).
- *Color — lower surface.*—Pale green (138A/138B) with central yellow-green vein (152A/152B).

Petiole:
- *Length.*—3.4-4.2 cm.
- *Diameter.*—About 2 mm.
- *Color.*—Green-yellow (152A/152B) under and reddish upper (183A).

Fruit:
- *Shape.*—Heart-shaped.
- *Diameter.*—32-34 mm.

*Height.*—28-32 mm.

*Weight.*—12-14 grams, average weight.

*Number per cluster.*—8-12 per spur.

*Skin color* (*include ground color and over color*).—Bright red (N186C) tending toward shiny purplish red (187A) at advanced maturity.

*Presence of lenticels.*—Yes.

*Density of lenticels.*—Medium.

*Skin thickness.*—Medium-thin.

*Skin texture.*—Medium.

*Anthocyanin coloration present near skin?.*—No.

*Tenacity of flesh to stone.*—Low.

*Flesh color.*—Rosé (52A).

*Flesh texture.*—Fine.

*Juiciness.*—High.

*Juice analysis* (*brix, acidity, tss, etc.*).—21.3° Brix and 13.9 g/l malic acid (2012 data).

*Stone size.*—Medium-large.

*Stone shape.*—Elliptical.

*Stone color.*—Pale brown (165D).

Fruit stem:

*Length.*—38-42 mm.

*Diameter.*—Just over 1 mm.

*Color.*—Green (143B.

Harvest:

*Maturity date range.*—Between June 5 and June 25, approximately 18-20 days after 'Burlat' and approximately 0-2 days after 'Bing'; optimum harvest dates for 'PA4UNIBO' are June 15 to June 20 in Modena Province.

*Harvest date range* (*if different*).—Same as above.

The diploid cultivar 'PA4UNIBO' is not self-fertile and has the allelic profile S3S4, requiring pollinators for optimum fruit load and yield. Pollinators for 'PA4UNIBO' include Sweet Aryana® ('PA1UNIBO*') (U.S. Plant Application Pending), Sweet Gabriel® ('PA3UNIBO*') (U.S. Plant Application Pending), Sweet Saretta® ('PA5UNIBO*') (U.S. Plant Application Pending), although other same-species pollinators are anticipated to be compatible and prove productive.

Under observation during planting, growing and harvesting under normal cultural and growing conditions in Modena Province, Italy, no particular insect or plant/fruit disease resistance or susceptibility has been observed.

Because of the outstanding and unique horticultural characters of the claimed plant, especially its long harvest period and large size, this cherry can be planted to extend the cultivar's season. Although this new variety of cherry possesses the above-described characteristics, it is to be understood that variations and fluctuations may occur in the magnitude and qualities due to changes in growing and climate conditions, irrigation, fertilization, pruning and pest control.

What is claimed is:

1. A new and distinct cherry tree as herein described and illustrated.

* * * * *